(12) United States Patent
Haverty

(10) Patent No.: US 8,246,924 B2
(45) Date of Patent: Aug. 21, 2012

(54) COMBUSTION PROCESS FOR THE MANUFACTURE OF CALCIUM PHOSPHATE AND CALCIUM PHOSPHATE COMPOSITE PARTICLES

(75) Inventor: Donncha Haverty, Nenagh (IE)

(73) Assignee: HKPB Scientific Limited (IE)

( * ) Notice: Subject to any disclaimer, the term of this patent is extended or adjusted under 35 U.S.C. 154(b) by 87 days.

(21) Appl. No.: 12/742,645

(22) PCT Filed: Nov. 12, 2008

(86) PCT No.: PCT/EP2008/065414
§ 371 (c)(1),
(2), (4) Date: Sep. 8, 2010

(87) PCT Pub. No.: WO2009/062973
PCT Pub. Date: May 22, 2009

(65) Prior Publication Data
US 2011/0008232 A1    Jan. 13, 2011

(30) Foreign Application Priority Data
Nov. 12, 2007   (IE) ................... 2007/0808

(51) Int. Cl.
*B01J 19/00*   (2006.01)
*C01B 15/16*   (2006.01)
*C01B 25/26*   (2006.01)
*C09C 1/02*    (2006.01)
*C23C 16/00*   (2006.01)
*F23L 7/00*    (2006.01)

(52) U.S. Cl. ........ 423/305; 423/308; 106/462; 422/129; 431/2; 427/255.25; 427/255.28; 427/255.38

(58) Field of Classification Search ............... 423/305, 423/308; 106/462; 422/129; 431/2; 427/255.25, 427/255.28, 255.38
See application file for complete search history.

(56) References Cited

U.S. PATENT DOCUMENTS

| | | | | |
|---|---|---|---|---|
| 4,836,994 A | * | 6/1989 | Inoue et al. | 423/308 |
| 5,205,928 A | * | 4/1993 | Inoue et al. | 210/198.2 |
| 2006/0110306 A1 | * | 5/2006 | Chow et al. | 423/301 |
| 2007/0092424 A1 | * | 4/2007 | Kobayashi et al. | 423/305 |

FOREIGN PATENT DOCUMENTS

WO    2005087660 A1    9/2005

OTHER PUBLICATIONS

Vallet-Regi, Maria, et al., "Calcium phosphates as substitution of bone tissues", Progress in Solid State Chemistry 32 (2004) pp. 1-31.
Loher, Stefan, et al., "Fluoro-apatite and Calcium Phosphate Nanoparticles by Flame Synthesis", Chem. Mater. 2005, 17. pp. 36-42.
Herrero, E., et al., "Influence of the Deposition Parameters on La-A-Mn-O (A=Ca. Sr) Films Grown by Low-Pressure Aerosol Pyrolysis", Chem. Mater, 1999, 11. pp. 3521-3527.

(Continued)

*Primary Examiner* — Timothy Vanoy
(74) *Attorney, Agent, or Firm* — Schwabe, Williamson & Wyatt, P.C.

(57) ABSTRACT

The present application is directed to methods of manufacturing calcium phosphate particles. In particular, the method is directed at eliminating the requirement for a sintering step in the manufacturing process. The method involves the atomization and combustion of one or more antecedent compositions containing calcium precursors, phosphorus precursors and hydrogen peroxide.

29 Claims, 2 Drawing Sheets

OTHER PUBLICATIONS

Habibovic, Pamela, et al., "Biomimetic Hydroxyapatite Coating on Metal Implants", Journal of the American Ceramic Society, vol. 85, No. 3., pp. 517-522 (2002).

Cabanas, M.V., et al., "Calcium phosphate coatings deposited by aerosol chemical vapour deposition", J. Mater. Chem., 2003, 13, pp. 1104-1107.

* cited by examiner

COMBUSTION PROCESS FOR THE MANUFACTURE OF CALCIUM PHOSPHATE AND CALCIUM PHOSPHATE COMPOSITE PARTICLES

CROSS REFERENCE TO RELATED APPLICATIONS

This application claims foreign priority benefit from Irish Patent Application No. 2007/0808 filed Nov. 12, 2007 which disclosure is incorporated herein by reference.

FIELD OF THE APPLICATION

The present application relates to processes for the manufacture of Calcium phosphate and Calcium Phosphate composite particles

BACKGROUND

Calcium phosphates are technologically significant in many areas. There is a wide range of calcium phosphate salts that exist at ambient conditions either as meta-stable or stable phases, the most common are listed in table 1 in order of increasing solubility[1] in aqueous solution. An amorphous calcium phosphate (ACP) phase has also been identified.

TABLE I

Common Calcium Phosphate Salts

| Chemical formula | Ca/P Ratio | Name |
| --- | --- | --- |
| $Ca_5(PO_4)_3(OH)$ | 1.67 | Hydroxyapatite (HAP) |
| $Ca_4H(PO_4)_3 \cdot 2.5H_2O$ | 1.33 | Octacalcium phosphate (OCP) |
| $Ca_3(PO_4)_2$ | 1.50 | Tricalcium phosphate (TCP) |
| $CaHPO_4 \cdot 2 H_2O$ | 1.00 | Dicalcium phosphate dihydrate (DCPD) |
| $Ca(H_2PO_4)_2$ | 0.50 | Monocalcium phosphate (MCP) |
| $Ca(H_2PO_4)_2 \cdot H2O$ | 0.50 | Monohydrate calcium phosphate (MCPH) |

Hydroxyapatite (HAP) is the most thermodynamically stable calcium phosphate salt at near ambient temperature and in the pH range 4 to 12. Significantly this includes physiological temperature and pH. HAP is used extensively in the catalysis, fertilizer and water treatment industries. It is also used in the biomedical and pharmacological arenas. Calcium phosphate-based biomaterials have been in use in medicine and dentistry for over 20 years because of their excellent biocompatibility with human tissues. Thus, hydroxyapatite has been widely used in dental implants, percutaneous devices, periodontal treatment, alveolar ridge augmentation, orthopedics, maxillofacial surgery, otolaryngology, and spinal surgery. The functionality of HAP as a biomaterial originates from its chemical and structural similarity to bone-apatite, the main inorganic component of the teeth and bones of invertebrates. HAP is a known osteoconductive material and is used both as a coating on metallic medical devices for hard-tissue arthroplasty and as a constituent in synthetic bone grafts and cements. HAP, being bio-mimetic, promotes bone in-growth and fixation invivo, a necessary attribute of any successful hard-tissue implant[2-3].

As a result of its intrinsic biocompatibility and the fact that many biologically species will readily adsorb on its surface, HAP is increasingly becoming the material of choice for the delivery of a wide range of therapeutic agents including antibiotics, growth factors and other regulatory and/or functional proteins involved in various genetic pathways of physiological significance). Habraken et. al. have written a comprehensive review of ceramic composite matrices as scaffolds for drug delivery, Calcium Phosphate and Calcium irected at eliminating the requirement for a sintering step in the manufacturing applications[5].

While extensively used in the hard tissue arena, the use of HAP as an alternative to polymers in drug delivery systems relevant to cardiovascular medical devices is currently under development for example MIV therapeutics VESTASYNC™ stent. Results recently reported on the clinical trial underway by MIV Therapeutics demonstrate no adverse clinical effects from the use of HAP-coated coronary stents[6].

In addition, hydroxyapatite has also been used as a biological chromatography support in protein purification and DNA isolation as in U.S. Pat. No. 4,798,886[7]. Hydroxyapatite is also currently used for fractionation and purification of a wide variety of biological molecules, such as subclasses of enzymes, antibody fragments, and nucleic acids[8]. Crystalline hydroxyapatite columns are commonly used in high-performance liquid chromatography. Typically, the chromatographic column is filled with irregularly shaped hydroxyapatite gels having poor mechanical strength.

It is known that spherical powders, in general, have better rheological properties than irregular powders and, thus, produce better coatings for hip implants and chromatographic separation. Spherical hydroxyapatite ceramic beads have recently been developed that exhibit improved mechanical properties and physical and chemical stability. However, these spherical ceramic beads are between 20-80 micron in size as in U.S. Pat. No. 5,858,318[9].

The electromechanical properties of HAP have recently attracted significant interest; in particular it has been shown that HAP is pyroelectric and possibly piezoelectric. Anecdotal evidence of the role of the electrical properties of HAP being of importance in physiological environment exists wherein polarised HAP has been shown to have improved bioactivity in simulated body fluid experiments as compared with its un-polarised counterpart. However to fully exploit the piezoelectric and or pyroelectric potential of HAP more controllable methods to manufacture single crystals and or anisotropic films or ceramic bodies of HAP are desirable.

Invitro, the response of osteoblasts (bone cells) to calcium phosphate particles or ceramics has been shown to be dependent on the topography and porosity of the materials at both the micro/meso and macro scales[10]. Furthermore the porosity and surface chemistry of calcium phosphate particles and ceramics also affects their functionality as drug carriers, in particular the surface area available for adsorption and the chemical nature of the surface itself determines the amount of therapeutic that can be loaded and the subsequent elution profile achieved invivo.

The demand for synthetic well characterised HAP is driven by these high end purification and invivo applications. Consequently, much time and effort has been devoted to developing processes to manufacture Calcium Phosphate particles and ceramic bodies with tailored morphologies, topographies and porosities depending on the requirements of a specific application with the fundamental chemistry of HAP and Calcium Phosphates in general receiving much attention.

Several methods of preparing HAP and or depositing it onto surfaces have been reported including solid-state reaction pathways, plasma techniques, hydrothermal methods, layer hydrolysis of other calcium phosphate salts and sol-gel reaction methods among others[11-17].

The synthesis of HAP via hydrothermal routes by precipitation from supersaturated aqueous solutions is advantageous due to its low cost but all routes used to date have produced HAP crystals with poor crystallinity, often non-stoichiometric in composition. The difficulty with the production of high purity HAP crystals arises from the low solubility of Calcium phosphate phases in general in the pH regions of interest and as a consequence of the complicated nature of the phase diagram of the aqueous $Ca^{2+}/HPO_4^{2-}$ system[1]. Many reaction schemes have been proposed that use salts other than oxides or phosphates as the source of Calcium for HAP precipitation most common among them Calcium chloride and Calcium Nitrate. These salts are more soluble in aqueous solution giving highly supersaturated solutions with respect to [Ca] but as well as introducing contamination Cl or $NO_3$ ions other possible contaminants are introduced with the $PO_4$ source or to buffer the solution. Routes have been determined using carbonates, hydrogen phosphates, ammonium salts, potassium and sodium hydroxides, nitrates, urea, and chlorides all of which are possible contaminants capable of being introduced into the precipitating system with the reactants. Contamination of HAP with these ions gives rise to significant deviations in the crystallographic characteristics of the precipitated material. Furthermore the supersaturation ($\sigma$) conditions that prevail in such systems means that many precursor meta-stable phases are formed en route to HAP involving complex precipitation dissolution reactions mediated by surface chemistry phenomena. OCP, DCPD, TCP and ACP (amorphous Calcium phosphate) are the most commonly observed (kinetically stable) phases depending on temperature and pH. In many instances thermal treatment of the precipitated Calcium phosphate is often required resulting in non-stoichiometric HAP usually associated with a loss of hydroxyl ions at high temperature.

The most desirable hydrothermal route to HAP from a purity point of view would be the use of $Ca(OH)_2$, CaO and $H_2O$, and phosphoric acid mixed in the correct ratio as this would negate contamination of the final product with other ions. Such a reaction scheme has been proposed[18] but as the solubility of CaO is high relative to the solubility of HAP local super-saturations in the range of 10-20 exist in the early stages of the reaction, furthermore a number of meta-stable solid phase are formed en route to the final product. As a result of the slow kinetics of the transformations of these phases to HAP exceedingly long reaction times and intricate washing procedures must be applied during the process.

Importantly the supersaturation conditions that prevail in typical HAP synthesis routes where surface mediated secondary nucleation dominates, means that synthetic HAP generated by such methods is often amorphous or nanocrystalline. Furthermore dense bodies made by sintering such HAP powders are isotropic in nature.

Many disclosures are present that use spray drying as a means to HAP or other calcium phosphate salts but in all cases post processing sintering must be applied to yield the desired product.

The sol-gel method of HAP manufacture offers a molecular-level mixing of calcium and phosphorus precursors, which is capable of improving the chemical homogeneity of the resulting HAP to a significant extent[19].

Generally synthesis by the sol-gel process involves the mixing of Ca and P precursors, dissolved in an appropriate solvent, such as to yield a solution with the correct Ca to P molar ratio, 1.67. The resulting solution is typically aged to allow formation of a sol and or to remove excess solvent at which point it is sintered at high temperature to initiate reaction between the Ca and P species present. Many variations on this basic theme are reported in the literature employing different Ca and P precursor materials, solvents sintering temperatures and durations[20-32]. The temperature that is required to form the apatitic structure depends largely on the chemical nature of the precursors but prolonged holding of the reactants at high temperature inevitably results in the degradation of the resulting HAP due to Hydroxyl loss.

The sol-gel process is also particularly versatile in that additional components can be incorporated to yield products with tailored composition. For example, substituted apatites can be manufactured by including appropriate amounts of the subsistent ions in the sol. Among the ions that are substituted into Calcium phosphates are silica, halogen ions, carbonate, magnesium, strontium, vanadium, arsenic, sulphate, alumina, zirconia and many others.

In addition the sol-gel process can be used to manufacture composite materials where the Calcium phosphate is present in conjunction with other phases. Materials have been made where Calcium Phosphate is present either as an adherent layer on a substrate or as a component in a composite body. Such compositions typically contain Titania, Silica, Alumina, Zirconia and other ceramics as separate phases[26, 27, 32-41].

While the sol-gel process has enjoyed a measure of success and offers a number of advantages, namely that it is cost effective and highly versatile, as a means to Calcium phosphate production its main draw back is the requirement of post reaction thermal processing. This inevitably gives rise to non-stoichiometric product (hydroxyl loss) and degradation of the desired product (HAP) to CaO and other Calcium phosphate salts. It is however clear from the literature that HAP precursor preparations that have a neutral or basic pH (often involving Ammonium Hydroxide) require higher sintering temperatures than those that are formed from acidic precursor sols such as the sol-gel preparations of Dean-Mo Liu et. al.[58]. However a disadvantage with acidic precursors is the lack of hydroxyl species in the precursor solutions for incorporation into the HAP lattice.

Methods of manufacturing composite blasting particles in which HAP is a component have also been disclosed for blasting purposes. In this instance the HA is present within a glassy matrix with other harder materials which give the particle mass and density allowing impregnation of the HAP component on impact. Such particles are created using sol-gel techniques and again require prolonged sintering during there manufacture. A number of disclosures revolve around shot peening processes involving composite particles comprised of a dense core material and an outer adherent layer of softer material, for example the Rocatek junior bonding system™ for dental implants. In this instance composite particles comprising a dense core of Alumina and an outer adherent layer of silica are employed in the shot blasting of metallic implants the outer adherent layer of silica embedding in the surface on impact. The silica so embedded allows enhanced adhesion of further polymer layers attached to the implants through the use of silane coupling chemistry. Similar type particles have been disclosed wherein the outer layer is composed of Titania. The generation of such stratified particles comprising a dense core with outer adherent layers of Calcium Phosphate would have similar applications in the biomedical field but to date no flame pyrolysis method to manufacture them has been disclosed.

Flame spray pyrolysis and or oxidation have received much attention in recent years as a means to industrial scale production of many important inorganic compounds including nanoparticles. Examples include processes for the manufacture of Carbon black, Titania, Zinc oxide and fumed Silica among others. Many metallic powders and catalysts are also produced in Aerosol flame reactors. In such reactors solutions of appropriate precursor compounds are injected into a high temperature flame to initiate chemical reaction and yield the desired product[42-52]. Flame spray reactors offer the advantage of being readily scalable to industrial production while simultaneously enabling a desired level of control over the morphology and size of the particles manufactured.

Such a scheme has recently been proposed for the manufacture of Calcium phosphate nano-particles including TCP and HAP[53]. In this disclosure a solution of appropriate Ca and P precursors present as carboxylates in an aqueous solution are injected into a high temperature flame fuelled by methane and oxygen to initiate reaction. The resultant products however required a further thermal processing step (sintering) to yield the desired products. Cho et al.[54] have also recently reported a spray pyrolosis process for the manufacture of Hydroxyapatite nano particles involving the injection of an aqueous solution of Ammonium Phosphate and Calcium Nitrate into a high temperature flame fuelled by propane. The resulting particles however required a further sintering step to yield the desired material. Inoue et al.[55-57] teach combustion processes for the production of calcium phosphate materials utilising a mixture of aqueous and hydrocarbon solvent containing Ca and P precursors injected into a flame to initiate reaction. However to achieve complete dissolution of the precursors in the solvent mixture significant amounts of water are used in conjunction with the hydrocarbon. Even so an excess of acid must be used to prevent the precipitation of non-desirable Ca and P phases in the precursor solution prior to exposure to the flame. Given that residence times in the flame are very low the presence of significant volumes of water in the precursor solution is disadvantageous: latent heat must be supplied to evaporate this water reducing the temperatures in the flame and kinetically hindering the extent of reaction. As a result the product produced while having the correct Ca/P ratio is amorphous and must be sintered to yield crystalline material.

SUMMARY

Flame synthesis processes that utilise mixed aqueous, hydrocarbon solvents suffer the problems outlined above and the present application is directed toward providing a combustion process that will yield crystalline Calcium Phosphate directly from a flame pyrolysis step without the requirement for additional sintering. This is achieved by using Hydrogen peroxide as a component in the precursor material. This provides a number of advantages and features that will become apparent from the following description and claims.

The present application teaches a method of manufacturing Calcium phosphate salts involving the direct combustion of a solution of suitable Ca and P precursor compounds dissolved in an appropriate solvent that is particularly suitable for the production of HAP. The process may also be used to manufacture composite particles and to deposit Calcium phosphate coatings on the surface of metallic and ceramic articles, particularly implants.

More particularly, the present application provides a method of manufacturing calcium phosphate materials, calcium phosphate particles produced by the method, an coated with the particles, a system for manufacturing and a system for coating in accordance with the claims which follow. Advantageous features, alternatives and embodiments are set forth in the dependent claims.

DESCRIPTION OF DRAWINGS

The present application will be understood more clearly with reference to the following drawings in which.

DETAILED DESCRIPTION

Figure 1:
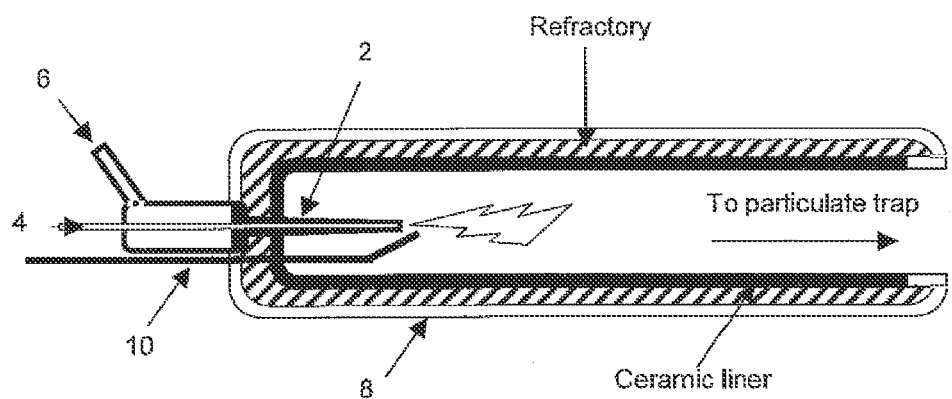
FIG. 1 is a schematic representation of an exemplary burner configuration for use in the present application.

The key to the successful manufacture of pure HAP from solutions or sols of Ca and P precursors, in the prior art, is the provision of high amounts of thermal energy to initiate reaction of the precursor compounds and crystallise the HAP lattice while simultaneously maintaining water and or hydroxyl species in the environment, impossible in any process that utilises prolonged high temperature sintering.

The present application circumvents this problem by removing the requirement for prolonged sintering of the products while providing sufficient thermal energy to initiate reaction of the precursors and simultaneously maintaining steam and hydroxyl species in the environment at the point of reaction.

Suitable Phosphorous and Calcium compounds are dissolved or suspended in an excess of flammable solvent in appropriate ratios to produce an antecedent composition of the calcium phosphate materials. Hydrogen peroxide is also added as a component in the combustion mixture.

It will be known to those skilled in the art that hydrogen peroxide may undergo the following reactions:

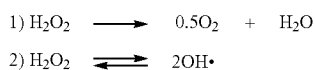

1) $H_2O_2 \longrightarrow 0.5O_2 + H_2O$

2) $H_2O_2 \rightleftharpoons 2OH\cdot$

The latter is responsible for increasing the oxidising power (the dissolving power) of acids and $H_2O_2$ is utilised in conjunction with mineral acids for this purpose in oxidising preparations such as piranha solution.

In the present application the presence of peroxide in the antecedent composition allows the water content of the antecedent composition to be kept to a minimum while preventing the precipitation of unwanted Ca and P phases in the composition prior to being fully mixed.

In addition reaction 2 provides a source of Hydroxyl species in the flame even though acidic conditions may prevail in the antecedent composition, particularly important in the production of HAP.

The former reaction provides the following advantages in the context of the present application:

Firstly the production of Oxygen in the flame aids complete combustion of the Hydrocarbon solvent and secondly the evolution of the gas aids in the atomisation of the antecedent composition being combusted. Also as this reaction is highly exothermic, additional heat is provided in the flame to counter balance the heat removed by the evaporation of the minimal aqueous component.

The antecedent compositions of the calcium phosphate materials and Hydrogen Peroxide are then atomised and mixed with an oxygen source preferably simultaneously, and ignited. The solvent preferably has a high calorific value and a sufficiently high molar composition of Hydrogen to provide both; the thermal energy to initiate reaction of the precursor compounds to yield the desired Calcium phosphate salt and steam as a by-product of the combustion reaction. In the particular case of HAP production maintaining a hydrated environment during the reaction is beneficial to yielding pure stoichiometric product.

The Calcium precursor material may be chosen from one or more soluble calcium salts including, by way of example, Calcium Nitrate, Calcium chloride, Calcium fluoride and Calcium iodide. The precursor Calcium compound may be chosen from one or more organo-calcium compounds including, by way of example, Calcium alkoxides ($Ca(OR)_2$) and other esters of Calcium. The organo-calcium precursor compound may also be obtained by dissolving a soluble calcium salt in an appropriate solvent. Furthermore the Calcium precursor may be chosen from one or more non-soluble Calcium salts including by way of example Calcium oxides, Calcium carbonates, Calcium hydrogen carbonates, Calcium sulphates and Calcium phosphates in the nanometer particle size range distributed in the solvent to form a colloid.

The Phosphorous precursor material may be chosen from one or more soluble Phosphatic salts including by way of example Phosphorous oxides, Ammonium Hydrogen Phosphate, Sodium Phosphates and Potassium Phosphates. Advantageously the Phosphorous precursor material may be chosen from one or more of Phosphorous acid and Phosphoric acid. The precursor Phosphorous compound may be chosen from one or more organo-Phosphatic compounds including by way of example Phosphatic alkoxides, Phosphatic phenoxides, Phosphite esters ($P(OR)_3$), Phosphate esters ($OP(OR)_3$), Phosphonic acids ($HOP(OR)_3$) or Phosphonates ($ROP(OR)_3$) where R is any aryl or alkyl group. The organo-Phosphatic precursor compound may also be obtained by dissolving a soluble Phosphatic salt or Phosphatic acid in an appropriate solvent. The Phosphorous precursor may be chosen from one or more non-soluble Phosphatic salts including by way of example Calcium Phosphate salts in the nanometer particle size range distributed in the solvent to form a colloid.

The solvent may comprise an alcohol including alkyl and aryl alcohols but more preferably an alkyl alcohol and most preferably methanol, ethanol, iso-propyl-alcohol (IPA) or 1-propanol. The solvent may also comprise a hydrocarbon including by way of example alkanes, alkenes, alkynes, aldehydes, esters or ketones with not more than 20 carbons per molecule but more preferably not more than 10 carbons per molecule and most preferably not more than 6 carbons per molecule. The solvent may also comprise not more than 40% by volume water and hydrogen peroxide.

Individual Ca and P precursor solutions may be mixed prior to being atomised and combusted or may be atomised separately and mixed in the flame.

In one arrangement, the Calcium precursor is dissolved in the solvent to yield a solution with a Calcium concentration in the range 0.0001 Molar (moles $Lt^{-1}$) to 10 Molar but more preferably in the range 0.001 Molar to 5 Molar and most preferably in the range 0.01 Molar to 1 Molar while the phosphorous precursor is dissolved in the solvent to yield a Ca:P Molar ratio in the range 0.45-1.8 but more preferably in the range 0.5-1.7.

In a further arrangement, the required solution is made by dissolving the Phosphorous and Calcium precursors separately and adding the resulting solutions together to yield a combustible solution with the desired concentrations of P and Ca.

Control over the calcium to phosphorous ratio in the antecedent compositions and by extension over the calcium phosphate material produced in the flame is of significant importance to the end product.

In one arrangement, the desired Calcium phosphate salt is HAP and the molar Ca:P ratio in the solution is 1.67 while in a further embodiment the desired Calcium Phosphate salt is TCP and the molar Ca:P ratio in the solution is 1.5.

In one arrangement, the desired Calcium Phosphate salt is substituted HAP having the general formula $Ca_{10-x}(A)_x(PO_4)_{6-y}(B)_y(OH)_{2-z}(C)_z$ where A is any divalent cation including but not limited to Ca, Mg, Sr, Ba, divalent transition metals and divalent lanthanides. B may be an anion including but not limited to Phosphate, Silicate, Arsenate, Titanate, Alumina, Sulphate, Carbonate, tetrahedral ions of Transition metals and Lanthanides particularly oxides. C may be a monovalent anion including but not limited to Hydroxyl, Hydrogen Carbonate, Nitrate, Fluorine, Chlorine, Bromine and Iodine. In certain applications precursors of the desired substituting species are dissolved in the solution to be combusted such as to yield substituted apatites with x in the range 0.001 to 10, y in the range 0.001 to 6 and z in the range 0.001 to 2. The precursors of the substituting species are halides, oxides, silicates, hydroxides, phosphates, carbonates, nitrates and sulphates of the substituting species as well as organic precursors including but not limited to silanes, alkoxides and esters of the substituting species. In such applications the molar concentrations of the Ca and P precursors in the solvent are adjusted accordingly to preserve charge neutrality in the substituted apatite formed on combustion of the solution or colloid.

The particle size of the Calcium Phosphate materials produced may be in the nanometer range. In a further application the solution to be combusted additionally contains a suspension of insoluble seed Calcium phosphate salt on which additional Calcium Phosphate will crystallise and grow on combustion of the colloid or suspension allowing the manufacture of Calcium Phosphate particles with larger particle sizes. The particles produced may be a coalescence of nanoparticles and have nanostructure and porosity. Such particles have application as therapeutic carriers.

The solvent to be combusted may additionally contain a suspension of core particles in the nanometer to micron size range. On combustion of this colloid or suspension the Calcium phosphate salt crystallises on the surface of the core particle to yield a composite particle with an outer adherent layer of Calcium phosphate. Core particles are chosen from those comprising silica, bio-glasses, alumina, titania, titanium oxides, carbides, zirconia, stainless steel shot and grits, ferritic steel, shot, grit and combinations thereof. In one embodiment the composite particles thus produced have application in shot-peening based surface treatments. The core particles may also be fluidised in, for example, in a separate gas stream and delivered into the trajectory of the combustible solution just prior to its ignition or into the flame produced on ignition of the combustible solution.

In another arrangement, the combustion of the antecedent composition of the calcium phosphate materials is carried out in a burner comprising an atomiser (nozzle), an ignition source (spark or pilot flame), an oxygen supply, and a combustion chamber. The atomisation and combustion of the solution or colloid may be achieved using a conventional commercially available burner such as commercial oil burners or commercially available bio-fuel burners including ethanol and methanol burners. Similarly the combustible fluid may be atomised in a conventional commercially available spray nozzle.

In another arrangement combustion of the solution or colloid is carried out in a more specifically designed burner 1 having a combustion chamber; schematically represented in FIG. 1, in which a coaxial nozzle 2 is used to atomise the combustible solution or colloid. More particularly, the solution 4 or colloid is delivered to a central venture of the coaxial nozzle. A high velocity gas flow 6 substantially rich in oxygen is delivered through an outer venturi simultaneously atomising the combustible solution or colloid and supplying oxygen for the combustion reaction. The high velocity (outer) gas flow may additionally contain water vapour. The gas flow may additionally contain an inert gas, Hydrogen, a low molecular weight volatile hydrocarbon or combinations thereof. The nozzle may be constructed so that at least the outer part of the coaxial nozzle is fabricated substantially of a ceramic or other refractory material including by way of example alumina, porcelain, carbide, silicon carbide, tungsten carbide, boron carbide and\or mullite.

In one configuration, the combustion chamber is sealed at the end of the chamber comprising the nozzle. Optionally, an additional gas flow (not shown) may be provided through an entrance to the combustion chamber behind the venturi of the nozzle so as to induce a cooling affect behind the venturi and create a positive pressure that directs the combustion products down the combustion chamber towards the opposing (open) end. In one embodiment the additional gas flow contains oxygen, air, inert gas, water vapour, fluidised core particles or combinations thereof.

The gas flows into the combustion chamber are selected to ensure that, at least, sufficient oxygen is supplied to the reacting system to substantially convert all carbon and hydrogen entering the system (either as hydrogen gas or as the hydrogen in the hydrocarbons) into carbon dioxide and water respectively (to achieve complete oxidation). The ignition of the reactants may be achieved by generating a spark in the vicinity of the atomised solution or colloid exiting the nozzle venturi. The spark may be generated by an igniter 10 for example a electric spark generator or pilot flame as would be familiar to those skilled in the art. One of ordinary skill in the art will appreciate the importance of maintaining the ratio of oxidant to fuel within the flammability limits of the fuel whether, solvent, hydrogen or volatile hydrocarbon so as to propagate and maintain a flame.

The wall 8 of the combustion chamber may be constructed of a suitable metal, including for example, steel, iron or aluminium. The inner face of the wall of the chamber may be suitably lined with a thermally insulating refractory material, for example a ceramic. Exemplary materials suitable for this purpose include but are not limited to porcelain, Mullite, fire cements, alumina, carbides such as silicon carbides, tungsten carbides and boron carbide. Additionally flexible or compressible refractory materials may be used in the interstitial between the outer metal and inner refractory to absorb thermal shock arising from the differing thermal expansion properties of the metal and inner refractory material. Suitable materials for this purpose include commercially available thermally insulating tapes, liners, rope, glass wool and cloths. In use, the temperature of the chamber and\or the thermal gradient along the combustion chamber may be controlled by means of a heating source, for example using electrical heating coils embedded in the refractory lining.

Suitably, the oxidising flame burns at a temperature in the range of at 300° C. to 2000° C.

The length of the combustion chamber is suitably selected such that the residence time of the product particles in a high temperature and or hydrated environment is sufficient to yield the desired product. The combustion chamber is not limited to a horizontal configuration, thus for example it may also be arranged vertically with the flue gases directed upwards into a collection chamber. The selection of the length of the chamber may be dependent to an extent on the linear velocity of the combustion products emanating from the flame. Those skilled in the art will appreciate how this parameter is dependent on the flow rates into the combustion chamber. Optimum flow rates and\or chamber dimensions may be determined by calculation or experiment.

An advantage of the above methods is that the resulting Calcium phosphate particles or composite particles do not generally require additional thermal sintering to yield the desired product.

To facilitate recovery of the product, the open end of the combustion chamber may be vented to a particle trap (not shown) to recover the product particles. The particle trap may be a conventional scrubber or dust collector. Similarly, the particle trap may employ a liquid phase, preferably water, to trap the product particles.

In another arrangement the stream of calcium phosphate material particles produced in the chamber may be directed at an article so that a coating of said calcium phosphate materials is formed on the article. The elevated temperatures needed to form the calcium phosphate materials aid in the formation of the coating by fusing said materials to the article surface. The coating process may be most conveniently performed in a modified combustion chamber which is configured to accept the article. The process is particularly suited to articles constructed of metal, ceramic or other materials capable of withstanding elevated temperatures. The article may be moved or rotated during the coating process to achieve an even coating of materials on the article as required. This movement or rotation may be controlled through the use of the like of stepper motors, 2 and 3 axis robots and automated control systems, all of which would be familiar to those skilled in the art.

Examples

Example 1

Figure 2:
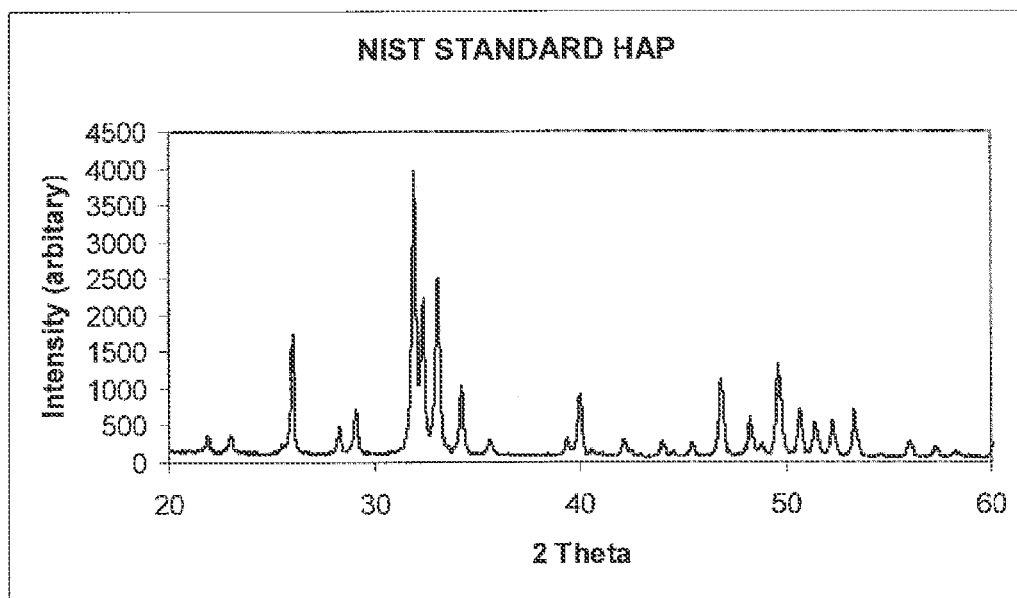
FIG. 2 is the XRD spectra of a HAP produced by methods in accordance with the prior art.
Figure 3:
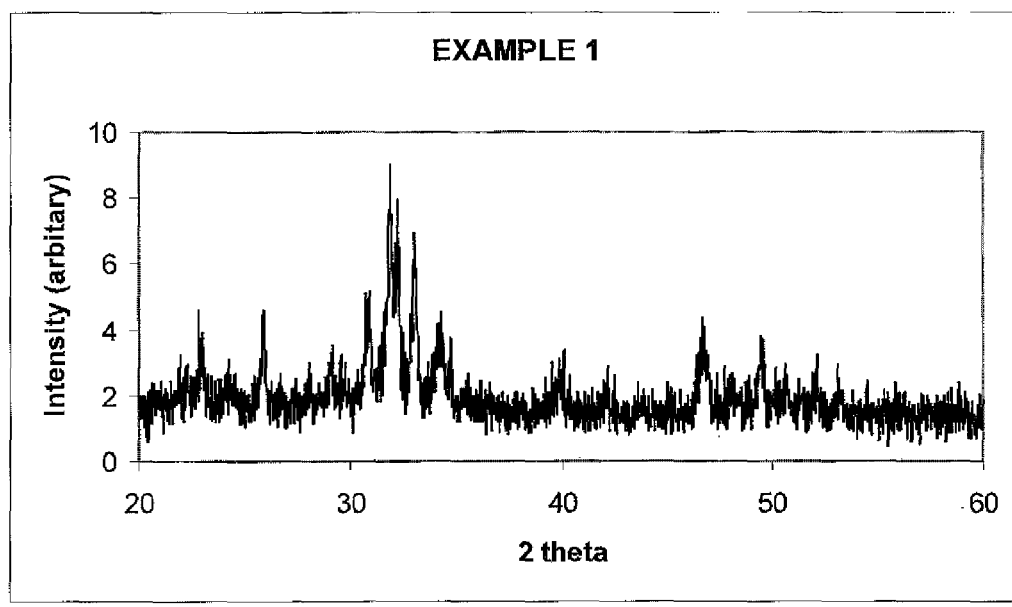
FIG. 3 is the XRD spectra of a Calcium Phosphate produced by direct combustion of a substantially dry ethanol/Ca and P precursor solution in accordance with the methods of the present application.

117.56 g of Calcium Nitrate tetra hydrate was dissolved in 250 ml of ethanol similarly 21.28 g of phosphorous pentoxide was dissolved in 250 ml of ethanol. The resulting solutions were mixed on complete dissolution of the salts and fed to an oil burner for combustion. The flue gases were directed into a stainless steel vessel containing water. After burning a powdered material was recovered form the water dried overnight at 100° C. and submitted for XRD (X-Ray Diffraction) analysis. The resulting XRD pattern is given in FIG. 3 and can be compared with that of the NIST standard HAP shown in FIG. 2. As indicated the burning of the ethanol solution having a molar Calcium to Phosphorous ratio of 1.67 resulted in the formation of HAP without further high temperature processing but peaks characteristic of TriCalcium Phosphate (TCP) and Calcium Oxide (CaO) are observed in the diffraction pattern.

Example 2

Figure 4:
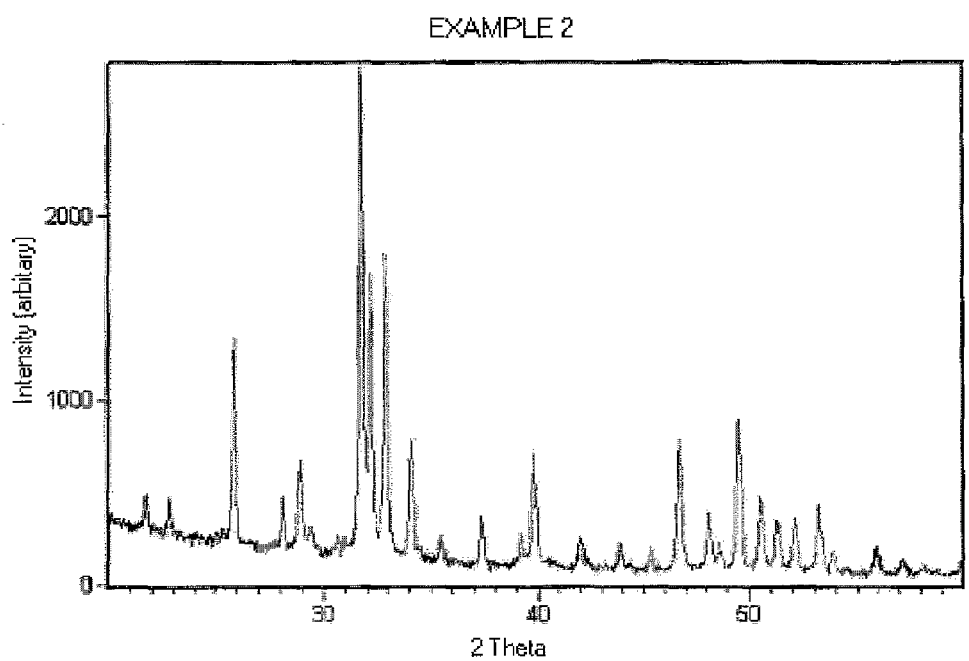
FIG. 4 is an XRD spectra of HAP produced by the methods of the present application.

A Calcium solution was made by dissolving 115.05 g of Calcium Nitrate tetra hydrate in 250 ml of ethanol. A phosphorus solution was made by adding 20 ml of 85% w/w aqueous Phosphoric acid to 50 ml of 30% w/w aqueous Hydrogen peroxide. The resulting solutions were mixed, adding the Calcium solution to the Phosphorus slowly with constant vigorous stirring. No precipitates were formed during or on the immediate mixing of the two solutions but subsequent to achieving the correct Ca/P ratio (complete mixing) turbidity did develop, the composition containing dispersed colloidal gelatinous material. This composition was feed to the inner venturi of a coaxial combustion nozzle. Air was supplied in the outer venturi and a pilot flame provided the means to ignite the atomised composition. The combustion products were directed into a stainless steel vessel containing water. After burning a powdered material was recovered form the water dried overnight at 100° C. and submitted for XRD (X-Ray Diffraction) analysis. The resulting XRD pattern is shown in FIG. 4. As indicated the burning of the ethanol/aqueous solution having a molar Calcium to Phosphorous ratio of 1.67 resulted in the formation of crystalline HAP without further high temperature processing Furthermore none of the peaks characteristic of TriCalcium Phosphate (TCP) and Calcium Oxide (CaO) are observed in the diffraction pattern demonstrating the advantage of the hydrogen peroxide.

CITED REFERENCES

1. Elliot, J. C., ed. Structure and chemistry of the apatites and other calcium orthophosphates. 1994, Elsevier: Amsterdam.
2. Chambers, B., S. F. St. Clair, and M. I. Froimson, Hydroxyapatite-Coated Tapered Cementless Femoral Components in Total Hip Arthroplasty. The Journal of Arthroplasty, 2007. 22(4, Supplement 1): p. 71-74.
3. Palm, L., et al., Acetabular Revision With Extensive Allograft Impaction and Uncemented Hydroxyapatite-Coated Implants. Results After 9 (7-11) Years Follow-Up. The Journal of Arthroplasty. In Press, Corrected Proof.
4. Lee, S.-H. and H. Shin, Matrices and scaffolds for delivery of bioactive molecules in bone and cartilage tissue engineering. Advanced Drug Delivery Reviews, 2007. 59(4-5): p. 339-359.
5. Habraken, W. J. E. M., J. G. C. Wolke, and J. A. Jansen, Ceramic composites as matrices and scaffolds for drug delivery in tissue engineering. Advanced Drug Delivery Reviews, 2007. 59(4-5): p. 234-248.
6. Abizaid, A. The MIV Polymer-Free Hydroxyapatite-Coated Sirolimus-Eluting Stent: First-in-Man Angiographic and IVUS Follow-Up Results. in Transcatheter Cardiovascular Therapeutics (TCT)2007. Washington, D.C.
7. Kato, K., Yamada, T. and Kawahara, K. (17 Jan. 1989) Mutual separation of proteins, U.S. Pat. No. 4,798,886
8. Kadoya, T., et al., High performance liquid chromatography of proteins on a hydroxyapatite column. J. Liquid Chromatography, 1988. 11: p. 2951-2967.
9. Luo, P. (12 Jan. 1999) Methods of synthesizing hydroxyapatite powders and bulk materials, U.S. Pat. No. 5,858,318
10. Hornez, J., et al., Biological and physico-chemical assessment of hydroxyapatite (HA) with different porosity. Biomol. Eng., 2007. November; 24(5): p. 505-9.
11. Cui, F. Z. and Z. S. Luo, Biomaterials modification by ion-beam processing. Surface and Coatings Technology, 1999. 112(1-3): p. 278-285.
12. Dorozhkin, S. V., A review on the dissolution models of calcium apatites. Progress in Crystal Growth and Characterization of Materials, 2002. 44(1): p. 45-61.
13. Mihailescu, I. N., et al., Calcium phosphate thin films synthesized by pulsed laser deposition: Physico-chemical characterization and in vitro cell response. Applied Surface Science, 2005. 248(1-4): p. 344-348.
14. Oner, M. and O. Dogan, Inhibitory effect of polyelectrolytes on crystallization kinetics of hydroxyapatite. Progress in Crystal Growth and Characterization of Materials, 2005. 50(1-3): p. 39-51.
15. Posner, A. S. and R. A. Beebe, The surface chemistry of bone mineral and related calcium phosphates. Seminars in Arthritis and Rheumatism, 1975. 4(3): p. 267-291.
16. Riman, R. E., et al., Solution synthesis of hydroxyapatite designer particulates. Solid State Ionics, 2002. 151(1-4): p. 393-402.
17. Yang, Y., K.-H. Kim, and J. L. Ong, A review on calcium phosphate coatings produced using a sputtering process—an alternative to plasma spraying. Biomaterials, 2005. 26(3): p. 327-337.
18. Markovic, M., B. Fowler, and M. Tung, Prepareration and comprehensive characterization of a Calcium Hydroxyapatite reference material. J. Res. Natl. Inst. Stand. Technol., 2004. 109(6): p. 553-568.
19. Ferraz, M. P., F. J. Monteiro, and C. M. Manuel, Hydroxyapatite nanoparticles: A review of preparation methodologies. Journal of Applied Biomaterials & Biomachanics, 2004. 2: p. 74-80.
20. Bezzi, G., et al., A novel sol-gel technique for hydroxyapatite preparation. Materials Chemistry and Physics, 2003. 78(3): p. 816-824.
21. Bigi, A., E. Boanini, and K. Rubini, Hydroxyapatite gels and nanocrystals prepared through a sol-gel process. Journal of Solid State Chemistry, 2004. 177(9): p. 3092-3098.
22. Bogdanoviciene, I., et al., Calcium hydroxyapatite, Ca10(PO4)6(OH)2 ceramics prepared by aqueous sol-gel processing. Materials Research Bulletin, 2006. 41(9): p. 1754-1762.
23. Chai, C. S., K. A. Gross, and B. Ben-Nissan, Critical ageing of hydroxyapatite sol-gel solutions. Biomaterials, 1998. 19(24): p. 2291-2296.
24. Cheng, K., et al., Sol-gel derived fluoridated hydroxyapatite films. Materials Research Bulletin, 2003. 38(1): p. 89-97.
25. Cheng, K., et al., Synthesis of hydroxyapatite/fluoroapatite solid solution by a sol-gel method. Materials Letters, 2001. 51(1): p. 37-41.
26. Cheng, K., et al., The effect of triethanolamine on the formation of sol-gel derived fluoroapatite/hydroxyapatite solid solution. Materials Chemistry and Physics, 2003. 78(3): p. 767-771.
27. Cheng, K., S. Zhang, and W. Weng, The F content in sol-gel derived FHA coatings: an XPS study. Surface and Coatings Technology, 2005. 198(1-3): p. 237-241.
28. Deptula, A., et al., Preparation of spherical powders of hydroxyapatite by sol-gel process. Journal of Non-Crystalline Solids, 1992. 147-148: p. 537-541.
29. Eshtiagh-Hosseini, H., M. R. Housaindokht, and M. Chahkandi, Effects of parameters of sol-gel process on the phase evolution of sol-gel-derived hydroxyapatite. Materials Chemistry and Physics, 2007. 106(2-3): p. 310-316.
30. Fathi, M. H. and A. Hanifi, Evaluation and characterization of nanostructure hydroxyapatite powder prepared by simple sol-gel method. Materials Letters, 2007. 61(18): p. 3978-3983.
31. Feng, W., et al., A simple sol-gel technique for preparing hydroxyapatite nanopowders. Materials Letters, 2005. 59(8-9): p. 916-919.

32. Gan, L. and R. Pilliar, Calcium phosphate sol-gel-derived thin films on porous-surfaced implants for enhanced osteoconductivity. Part I: Synthesis and characterization. Biomaterials, 2004. 25(22): p. 5303-5312.
33. Andersson, J., et al., Sol-gel synthesis of a multifunctional, hierarchically porous silica/apatite composite. Biomaterials, 2005. 26(34): p. 6827-6835.
34. Balamurugan, A., et al., Electrochemical and structural characterisation of zirconia reinforced hydroxyapatite bioceramic sol-gel coatings on surgical grade 316L SS for biomedical applications. Ceramics International, 2007. 33(4): p. 605-614.
35. Balamurugan, A., et al., In vitro biological, chemical and electrochemical evaluation of titania reinforced hydroxyapatite sol-gel coatings on surgical grade 316L SS. Materials Science and Engineering: C, 2007. 27(1): p. 162-171.
36. Balamurugan, A., et al., Elaboration of sol-gel derived apatite films on surgical grade stainless steel for biomedical applications. Materials Letters, 2006. 60(17-18): p. 2288-2293.
37. Balamurugan, A., S. Kannan, and S. Rajeswari, Synthesis of hydroxyapatite on silica gel surface by using glycerin as a drying control chemical additive. Materials Letters, 2003. 57(7): p. 1244-1250.
38. Ballarre, J., et al., Protective hybrid sol-gel coatings containing bioactive particles on surgical grade stainless steel: Surface characterization. Applied Surface Science, 2007. 253(17): p. 7260-7264.
39. Ben-Nissan, B., A. Miley, and R. Vago, Morphology of sol-gel derived nano-coated coralline hydroxyapatite. Biomaterials, 2004. 25(20): p. 4971-4975.
40. Cheng, K., S. Zhang, and W. Weng, Sol-gel prepared [beta]-TCP/FHA biphasic coatings. Thin Solid Films, 2006. 515(1): p. 135-140.
41. Cheng, K., et al., The interfacial study of sol-gel-derived fluoridated hydroxyapatite coatings. Surface and Coatings Technology, 2005. 198(1-3): p. 242-246.
42. Aromaa, M., H. Keskinen, and J. M. Makela, The effect of process parameters on the Liquid Flame Spray generated titania nanoparticles. Biomolecular Engineering. In Press, Corrected Proof: p. 943.
43. Camenzind, A., R. Strobel, and S. E. Pratsinis, Cubic or monoclinic Y2O3:Eu3+ nanoparticles by one step flame spray pyrolysis. Chemical Physics Letters, 2005. 415(4-6): p. 193-197.
44. Chang, H., et al., Synthetic routes for titania nanoparticles in the flame spray pyrolysis. Colloids and Surfaces A: Physicochemical and Engineering Aspects. In Press, Corrected Proof: p. 187.
45. Chang, H., J.-H. Park, and H. D. Jang, Flame synthesis of silica nanoparticles by adopting two-fluid nozzle spray. Colloids and Surfaces A: Physicochemical and Engineering Aspects. In Press, Corrected Proof: p. 187.
46. Ernst, F. O., et al., Electrochemically active flame-made nanosized spinels: LiMn2O4, Li4Ti5O12 and LiFe5O8. Materials Chemistry and Physics, 2007. 101(2-3): p. 372-378.
47. Fennell, P. S., J. S. Dennis, and A. N. Hayhurst, The sampling of nanoparticles of MgO formed when doping an oxygen-rich flame with magnesium: The measurement of the concentrations and size-distributions of these nanoparticles. Combustion and Flame. In Press, Corrected Proof: p. 943.
48. Haider, P. and A. Baiker, Gold supported on Cu—Mg—Al-mixed oxides: Strong enhancement of activity in aerobic alcohol oxidation by concerted effect of copper and magnesium. Journal of Catalysis, 2007. 248(2): p. 175-187.
49. Jang, H. D., et al., Synthesis of SiO2 nanoparticles from sprayed droplets of tetraethylorthosilicate by the flame spray pyrolysis. Current Applied Physics, 2006. 6(Supplement 1): p. e110-e113.
50. Jang, H. D., et al., Synthesis and characterization of indium-tin oxide (ITO) nanoparticles. Current Applied Physics, 2006. 6(6): p. 1044-1047.
51. Jang, Y. J., C. Simer, and T. Ohm, Comparison of zinc oxide nanoparticles and its nano-crystalline particles on the photocatalytic degradation of methylene blue. Materials Research Bulletin, 2006. 41(1): p. 67-77.
52. Madler, L., et al., Controlled synthesis of nanostructured particles by flame spray pyrolysis. Journal of Aerosol Science, 2002. 33(2): p. 369-389.
53. Stark, W. J. (23 Aug. 2007) Flame synthesis of metal salt nanoparticles, in particular calcium and phosphate comprising nanoparticles United States of America Patent Application 20070196259
54. Cho, J. S. and Y. C. Kang, Nano-sized hydroxyapatite powders prepared by flame spray pyrolysis. J. Alloys Compd, 2007. doi:10.1016/j.jallcom.2007.09.092.
55. Inoue, S. and Ono, A. (8 Dec. 1987) Calcium-phosphorus-apatite having novel properties and process for preparing the same, U.S. Pat. No. 4,711,768
56. Inoue, S. and Ono, A. (6 Jun. 1989) Calcium-phosphorus-apatite having novel properties and process for preparing the same, U.S. Pat. No. 4,836,994
57. Inoue, S., Ono, A. and Otaki, N. (28 Apr. 1992) Process for the preparation of microspherical sintered bodies of hydroxyapatite and a chromatographic packing material comprising the microspherical sintered bodies of hydroxyapatite, U.S. Pat. No. 5,108,956
58. Dean-Mo Liu et. al. (2001) 'Water-based sol-gel synthesis of Hydroxyapatite: process development' *Biomaterials*, 22, pg 1721-1730.

The invention claimed is:
1. A method of manufacturing a stable or meta-stable calcium phosphate phase, the method comprising:
    atomisation of one or more antecedent compositions containing calcium precursors, phosphorus precursors, and hydrogen peroxide; and
    combustion of the atomised one or more antecedent compositions.
2. The method of claim 1 wherein the calcium phosphate phase comprises one or more of:
    a. calcium phosphate particles, and
    b. calcium phosphate composite particles.
3. The method of claim 1 wherein the calcium phosphate phase comprises a calcium phosphate material mixed with at least one other material.
4. The method of claim 1 wherein the calcium phosphate phase comprises a coating of calcium phosphate materials around an inner core particle.
5. The method of claim 1 wherein the one or more antecedent compositions comprise one or more of:
    a. a liquid,
    b. a solution,
    c. a suspension,
    d. a gel,
    e. a sol,
    f. a colloid,
    g. particulate, and
    h. gas(es).

6. The method of claim 1 wherein the one or more antecedent compositions comprise one or more of:
   a. organo-metallics,
   b. ionic species,
   c. particulate,
   d. water, and
   e. hydrocarbon.

7. The method of claim 6 wherein the one or more antecedent compositions comprise organo-metallics selected from alkoxides, carboxylates, and esters of one or more of:
   a. calcium,
   b. phosphorous,
   c. yttrium,
   d. zirconium,
   e. magnesium,
   f. silicon,
   g. strontium,
   h. barium,
   i. divalent transition metals, and
   j. divalent lanthanides.

8. The method of claim 6 wherein the one or more antecedent compositions comprise ionic species comprising one or more of: calcium, phosphorous, silicon, zirconium, yttrium, titanium, aluminium, phosphate, phosphite, nitrate, halide, oxide, hydroxide, carbonate, sulphate, silicate, arsenate, titanate, alumina, tetrahedral ions of transition metals, and tetrahedral ions of lanthanides.

9. The method of claim 1 wherein a mixing step is performed prior to atomisation and combustion to mix the one or more antecedent compositions together.

10. The method of claim 1 wherein the one or more antecedent compositions are mixed together during atomisation and\or combustion.

11. The method of claim 1 wherein the atomisation is performed by one or more of: Bernoulli atomizers, pressure atomisers, two-fluid atomisers, ultrasonic atomisers, modified spray dryers, modified spray coaters, airbrushes, electro spray atomisers, coaxial nozzle assemblies, nozzles incorporating a pressure drop, and coaxial nozzle assemblies operating on a gas lens principle.

12. The method of claim 1 wherein a gas is supplied to facilitate combustion.

13. The method of claim 12 wherein the gas comprises one or more of:
   a. hydrogen,
   b. oxygen,
   c. air,
   d. inert non-combustible gases,
   e. a volatile hydrocarbon, and
   f. water vapor.

14. The method of claim 12 wherein the gas additionally performs one or more of:
   a. atomisation, and
   b. delivery of particulate into a flame.

15. The method of claim 1 wherein the one or more antecedent compositions comprise particulate selected from one or more of: calcium phosphate, zirconia, stabilised zirconia, titania, alumina, glass, silica, carbon fibre, nitrides, sulphates, and carbides.

16. The method of claim 1 wherein the one or more antecedent compositions are combusted in a combustion chamber.

17. The method of claim 16 wherein walls of the combustion chamber comprise one or more of:
   a. metal, and
   b. refractory material.

18. The method of claim 17 wherein the walls of the combustion chamber comprise a heating source configured to control a thermal gradient along the combustion chamber.

19. The method of claim 1, further comprising collecting the calcium phosphate phase in one of:
   a. a scrubber,
   b. a dust collector, or
   c. a particle trap that employs a liquid to trap product particles.

20. The method of claim 1 wherein combustion is initiated by:
   a. a spark generator, or
   b. a pilot flame.

21. The method of claim 1 wherein the calcium phosphate phase comprises one or more of:
   a. hydroxyapatite,
   b. oxyapatite,
   c. carbonateapatite,
   d. fluoroapatite,
   e. chlororapatite,
   f. bromoapatite,
   g. tricalcium phosphate,
   h. octacalcium phosphate,
   i. dicalcium phosphate,
   j. monocalcium phosphate,
   k. amorphous calcium phosphate,
   l. calcium oxide in combination with phosphorous pentoxide, and
   m. calcium pyrophosphate.

22. The method of claim 1 wherein the calcium phosphate phase comprises substituted-apatites having the general formula $Ca_{10-x}(A)_x(PO_4)_{6-y}(B)_y(OH)_{2-z}(C)_z$, where
   A is a divalent cation comprising at least one of Ca, Mg, Sr, Ba, Y, Zr, Sm, divalent transition metals, and divalent lanthanides,
   B is an anion comprising at least one of phosphate, silicate, arsenate, titanate, aluminate, sulphate, carbonate, tetrahedral ions of transition metals, and tetrahedral ions of lanthanides,
   C is a monovalent anion comprising at least one of hydroxyl, carbonate, hydrogen carbonate, nitrate, fluoride, chloride, bromide, and iodide,
   x is in the range 0.001 to 10,
   y is in the range 0.001 to 6, and
   z is in the range 0.001 to 2.

23. Calcium phosphate particles as manufactured by the method of claim 1.

24. An object having a coating comprising material produced by the method of claim 1.

25. A system for manufacturing a stable or meta-stable calcium phosphate phase, the system comprising:
   a combustion chamber;
   a source of antecedent compositions, the antecedent compositions comprising calcium precursors, phosphorus precursors, and hydrogen peroxide;
   an atomiser for atomising the antecedent compositions into a stream comprising the antecedent composition; and
   an igniter for initiating combustion of the stream of atomised antecedent compositions.

26. The system of claim 25, wherein the combustion chamber is sealed at one end.

27. The system of claim 26, where the atomiser is arranged to direct the stream in a direction away from the sealed end.

28. The system of claim 25, further comprising means for introducing a further stream carrying particles.

29. A system for coating an article comprising a system according to claim 25, wherein the article to be coated is placed in a path of products arising from the combustion.

* * * * *